United States Patent [19]

Gradeff et al.

[11] 4,153,633
[45] May 8, 1979

[54] PROCESS FOR PREPARING METHYL HEPTENONE BY REACTION OF PRENYL-SUBSTITUTED METHYL PENTENONES WITH A POLY-FUNCTIONAL AMINE

[75] Inventors: Peter S. Gradeff, Andover, N.J.; Marshall R. Angeles, Rego Park, N.Y.

[73] Assignee: Rhodia, Inc., New York, N.Y.

[21] Appl. No.: 855,575

[22] Filed: Nov. 29, 1977

[51] Int. Cl.$^2$ ............................................. C07C 49/20
[52] U.S. Cl. ................................................. 260/593 R
[58] Field of Search ................................... 260/593 R

[56] References Cited

U.S. PATENT DOCUMENTS

| | | | |
|---|---|---|---|
| 3,976,700 | 8/1976 | DeSimone | 260/593 R |
| 3,983,175 | 9/1976 | Tamai et al. | 260/593 R |

*Primary Examiner*—Joseph E. Evans

[57] ABSTRACT

A process is provided for preparing methyl heptenone by reacting a ketone mixture comprising prenyl-substituted methyl pentenones with a polyfunctional amine, optionally in the presence of an inorganic alkali. The yield of methyl heptenone can be increased by hydrolysis of the reaction product with water.

34 Claims, No Drawings

PROCESS FOR PREPARING METHYL HEPTENONE BY REACTION OF PRENYL-SUBSTITUTED METHYL PENTENONES WITH A POLY-FUNCTIONAL AMINE

U.S. Pat. No. 3,668,255, patented June 6, 1972 to Meuly and Gradeff, provides a process for the alkylation of aliphatic ketones having an alpha hydrogen, substitution occurring on the carbon alpha to the carbonyl group, by use of solid alkali in the presence of an organic amine and/or ammonia as a catalyst. The reaction products are alkenyl highly branched ketones having a pleasant odor, useful in the formulation of perfumes and perfume bases. Many of these ketones are prepared for the first time by this process.

The process is particularly useful for the preparation of methyl heptenone. If acetone is reacted with 1-chloro-3-methyl-2-butene, good yields of methyl heptenone are obtained. However, the methyl heptenone is accompanied by a higher boiling ketone fraction, that constitutes a considerable proportion of the reaction product. In Example 27 of the patent, for example, the yield included 86 grams of crude methyl heptenone and 42 grams of the higher ketone residue, and the crude methyl heptenone only comprised 72% methyl heptenone. Economic application of this process to the preparation of methyl heptenone clearly requires conversion of the higher boiling ketone fraction into a useful product.

Analysis of the higher boiling ketone fraction has shown that it is a mixture containing large amounts of isomeric ketones of the following structure:

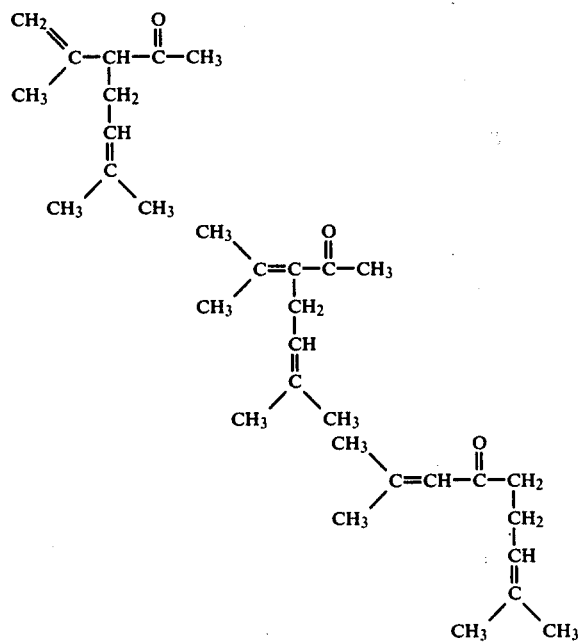

Acetone under the reaction conditions forms also some diacetone alcohol and mesityl oxide, and these then react with the prenyl chloride to produce the above isomers of prenyl mesityl oxide, also called prenyl-substituted methyl pentenones, in the same manner as acetone reacts with prenyl chloride to produce methyl heptenone. It is also possible that prenyl chloride reacts with the diacetone alcohol in the same manner to give the corresponding hydroxy derivatives that subsequently dehydrate. The presence of such hydroxy ketones is observed in the residues of the methyl heptenone production by the process of U.S. Pat. No. 3,668,255.

German patent No. 875,512 to Binapfl, ausgegeben May 4, 1953, proposed the hydrolysis of unsaturated ketones having a carbonyl group in the vicinity of an ethylenically unsaturated group by heating in the presence of water with the addition of acid, particularly weak acid, such as boric acid, adipic acid and benzoic acid. Rupture of the ketone molecule follows addition of water at the ethylenic linkage, and the product is a mixture of ketones and aldehydes. The process is indicated as applicable to aromatic and cycloaliphatic ketones, such as 1-cyclohexylidene-cyclohexanone-2 and 1-oxy-1,3-diphenyl-2-butylene.

German patent No. 927,688 to Stichnoth, ausgegeben May 16, 1955, suggested the conversion of o-cyclohexylidene-cyclohexanone to cyclohexanone, using water, in the presence of a small amount of alkali, at elevated temperatures.

German patent No. 946,443 to Wolf, published Feb. 2, 1956, proposed modification of the process of patent No. 875,512 by the use of alkali rather than acid. As the alkali, alkali metal hydroxides such as potassium and sodium hydroxide, as well as alkali metal compounds such as their carbonates, was suggested, as well as alkaline earth metal hydroxides such as calcium hydroxide. The process was indicated as applicable to cycloaliphatic and aromatic ketones, such as 1-cyclohexenyl-cyclohexanone-2- and acetophenone.

In accordance with U.S. Pat. No. 3,976,700 to DeSimone patented Aug. 24, 1976, the higher boiling ketone mixture of U.S. Pat. No. 3,668,255, containing prenyl-substituted methyl pentenones, is converted to methyl heptenone by hydrolytic cracking in the presence of alkali and water at a temperature within the range from about 50 to about 350° C. The resulting increased yield of methyl heptenone makes the production of methyl heptenone from acetone quite attractive commercially.

The process of U.S. Pat. No. 3,976,700 makes it possible to prepared methyl heptenone from mesityl oxide. Mesityl oxide is reacted with prenyl chloride at a temperature within the range from about −20° to about 150° C. in the presence of a solid alkali metal hydroxide selected from the group consisting of potassium hydroxide, sodium hydroxide, and mixtures thereof, and as a catalyst a nitrogen compound which is selected from the group consisting of ammonia, and aliphatic, cycloaliphatic, and heterocyclic hydrocarbon amines having from one to about sixty carbon atoms, such hydrocarbon amines containing hydroxy substituents, such hydrocarbon amines containing carboxylic acid substituents, and such hydrocarbon amines containing nitro substituents, the amounts of the mesityl oxide and prenyl chloride being in the molar ratio of from about 1:5 to about 20:1, the alkali hydroxide being in the proportion of from about 1 to about 2 moles per mole of prenyl chloride, and the amount of nitrogen compound being within the range from about 0.003 mole to about 1 mole per mole of prenyl chloride; thereby forming and separating a prenyl-substituted methyl pentenone mixture. The ketone mixture is subjected to hydrolytic cracking with water in the presence of alkali at a temperature within the range from about 50 to about 350° C., forming methyl heptenone, which is recovered from the resulting reaction mixture.

The process as applied to mesityl oxide is thus carried out in two steps, with or without intermediate purification of the ketone mixture prior to hydrolytic cracking, in accordance with the following reaction scheme:

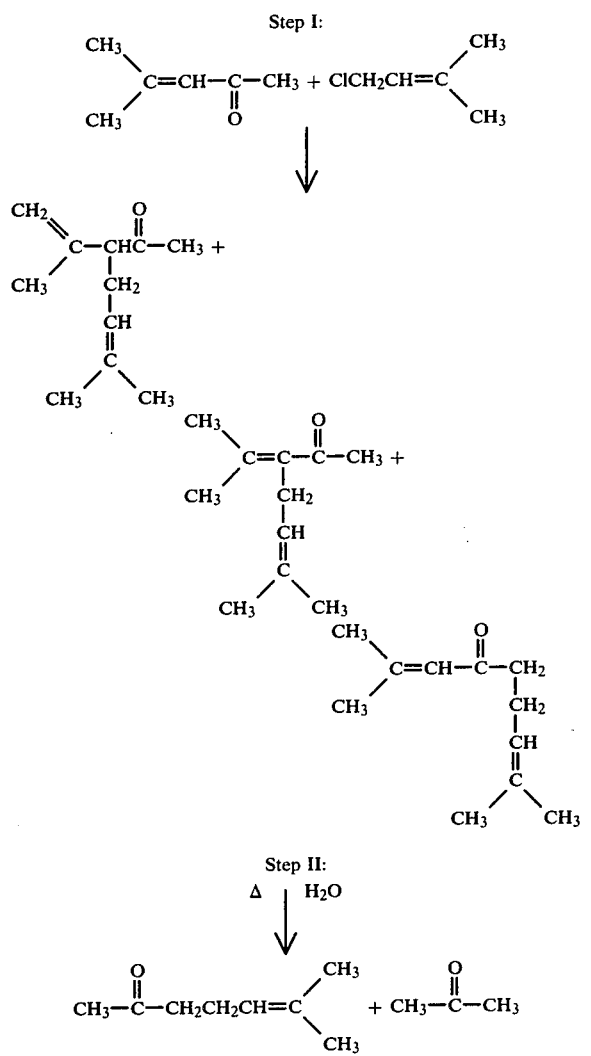

U.S. Pat. No. 3,976,700 also provides a process for preparing methyl heptenone from acetone. Acetone is reacted with prenyl chloride at a temperature within the range from about −20° to about 150° C. in the presence of a solid alkali metal hydroxide selected from the group consisting of potassium hydroxide, sodium hydroxide, and mixtures thereof, and as a catalyst a nitrogen compound which is selected from the group consisting of ammonia, and aliphatic, cycloaliphatic, and heterocyclic hydrocarbon amines having from one to about sixty carbon atoms, such hydrocarbon amines containing hydroxy substituents, such hydrocarbon amines containing carboxylic acid substituents, and such hydrocarbon amines containing nitro substituents, the amounts of the acetone and prenyl chloride being in the molar ratio of from about 1:5 to about 20:1, the alkali hydroxide being in the proportion of from about 1 to about 2 moles per mole of prenyl chloride, and the amount of nitrogen compound being within the range from about 0.003 mole to about 1 mole per mole of prenyl chloride. Methyl heptenone is recovered from the reaction mixture, preferably by distillation. The residual ketonic mixture comprising prenyl-substituted methyl pentenones is then subjected to hydrolytic cracking with water in the presence of alkali at a temperature within the range from about 50 to about 350° C.; forming additional methyl heptenone, which is recovered from the hydrolytic reaction mixture.

The process when starting with acetone is thus carried out in two steps, with separation of methyl heptenone produced in the first step before hydrolytic cracking of the prenyl-substituted methyl pentenones that are obtained as a by-product in the first step, in accordance with the following reaction scheme:

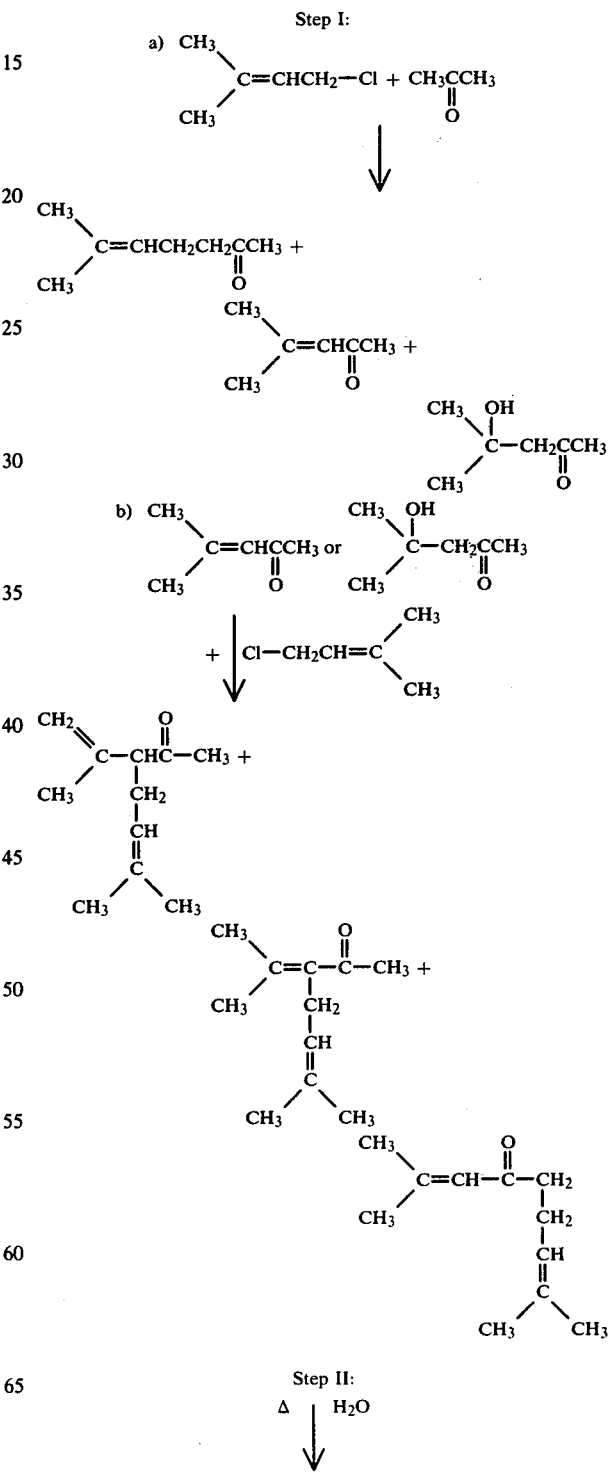

Step I:

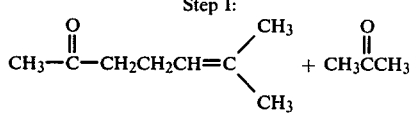

The hydrolytic cracking reaction of Step II with water and alkali is preferably carried out at elevated temperatures, and in a pressure vessel. The reaction can be conducted over a wide temperature range, within the range from about 50° to about 350° C., and preferably within the range from about 230° to about 310° C.

U.S. Pat. No. 3,976,700 also discloses that addition of acetone or other low-boiling aliphatic ketone otherwise stable under the reaction conditions increases the reaction rate considerably, and permits completion of the cracking in a very short time, ranging from about one minute to about one hour. The aliphatic ketones useful for this purpose contain from about three to about ten carbon atoms, in a straight or branched chain. The patent further states that the same effect on the reaction rate is exerted by lower aliphatic alcohols such as methanol, ethanol, isopropanol, butanol, isobutanol, amyl and isoamyl alcohol, as well as prenyl alcohol. No explanation is offered for the enhanced rate, which appears to be a solvent effect.

In accordance with the invention of Ser. No. 813,381 filed July 6, 1977, a process is provided for preparing methyl heptenone from a ketone mixture comprising prenyl-substituted methyl pentenones, which comprises subjecting the ketone mixture to hydrolytic cracking in the presence of an amine catalyst, water, and optionally an inorganic alkali, at a temperature within the range from about 10° to about 350° C., and recovering methyl heptenone from the hydrolytic reaction mixture.

In accordance with the present invention, a process is provided for preparing methyl heptenone by reacting a ketone mixture comprising prenyl-substituted methyl pentenones with a polyfunctional amine of the class of Ser. No. 813,381, optionally in the presence of an inorganic alkali. In the course of the reaction methyl heptenone and a mixture of methyl heptenone imine, acetone imine, and other imines such as prenyl mesityl oxide imine is formed. Hydrolysis of the reaction mixture with water decomposes the methyl heptenone imine, acetone imine and prenyl mesityl oxide imine to the free ketone, regenerating the amine starting material, and improving the yield of methyl heptenone.

The reaction mechanism is believed to involve amine adduct and imine formation and decomposition in accordance with the following reaction scheme:

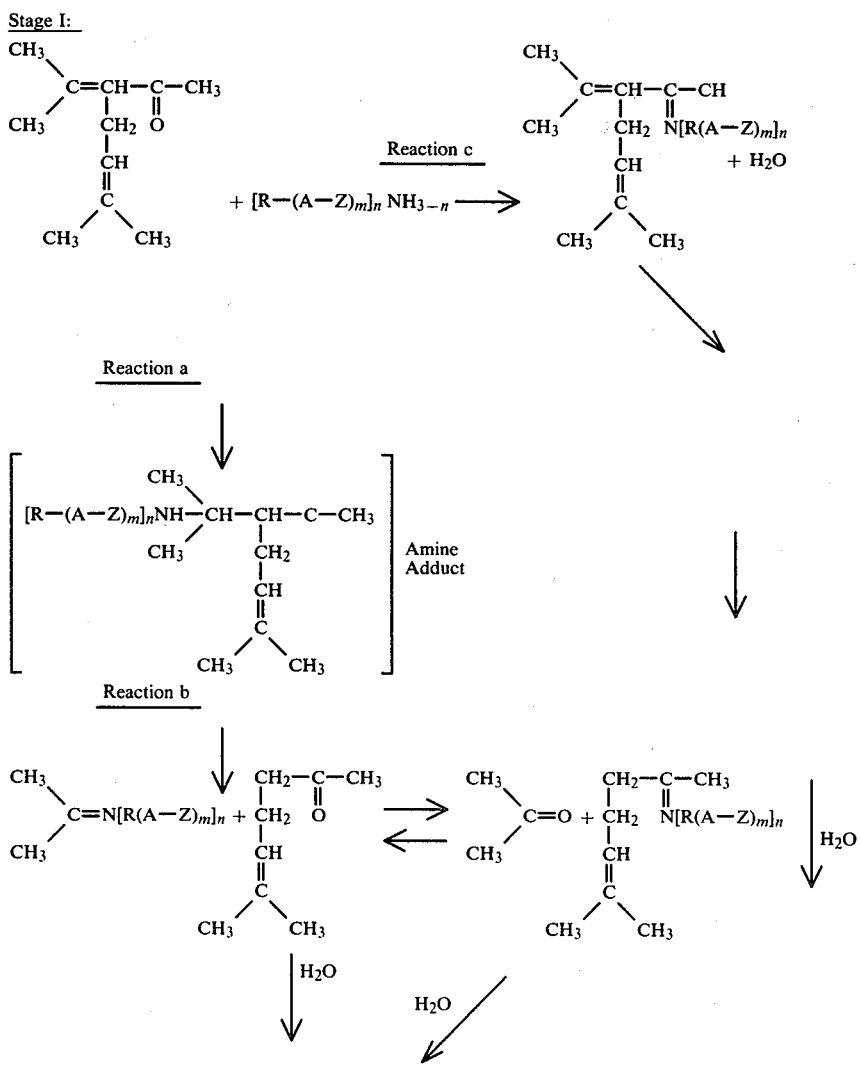

Stage I:

Stage II:

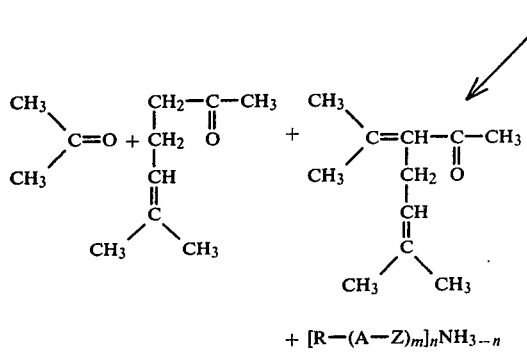

+ [R—(A—Z)$_m$]$_n$NH$_{3-n}$

The amine reaction product or adduct of Stage I is represented in brackets because it has not been isolated, and if it is formed is unstable, and decomposes (Reaction b) to form the products shown. Its presence is postulated as an explanation of the reaction, but if it is not formed, and the reaction has an entirely different and unknown mechanism, the process of the invention is unaffected, since the desired methyl heptenone reaction product is nonetheless obtained, and in excellent yield overall.

However, the imine and ketone products of its decomposition have been identified as present in the reaction mixture. The ratio of free ketones to imines varies, depending on the conditions.

In Stage II of the synthesis the imines are hydrolyzed by water to regenerate the corresponding ketones: methyl heptenone, acetone, and prenyl-substituted methyl pentenones, and the original amine. The amine can be recovered and recycled again and again.

As indicated above, a side reaction Reaction c takes place concurrently with the main Reaction a. To a certain extent the prenyl-substituted methyl pentenones react with the amine to form the corresponding imine instead of forming the amine adduct. Hydrolysis with water regenerates the prenyl-substituted methyl pentenones, which can be recycled. This side reaction therefore does not affect the final yield of methyl heptenone. The reaction is suppressed in the presence of a small amount of an inorganic base in Stage I thus enhancing the efficiency of the process.

The prenyl-substituted methyl pentenones exist as conjugated and nonconjugated isomers of the following structures:

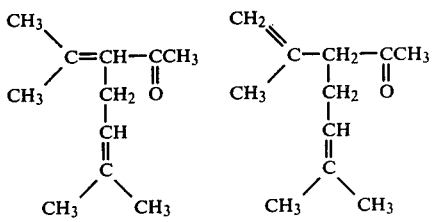

It is believed that the main Reaction a represented in Stage I involves the conjugated prenyl-substituted methyl pentenone isomer while the nonconjugated isomer tends to form the corresponding imine Reaction c. In the process of the reaction or during the hydrolysis of prenyl mesityl oxide imine the nonconjugated prenyl mesityl oxide tends to isomerise into the conjugated form.

Thus, removal of the conjugated isomer in the reaction may displace an equilibrium between the two isomers, and therefore the isomeric prenyl-substituted methyl pentenone mixtures containing the conjugated isomer that undergoes the reaction can be used as well as the pure conjugated isomer per se.

The polyfunctional amine has at least two functional groups, of which at least one group is an amine group and the other group can be another amine group, a hydroxyl group or an alkoxyl group. More than two functional groups such as three, four or five can be present.

The class of amines useful in the process in accordance with the invention is defined by the following formula:

[R—(A—Z)$_m$]$_n$NH$_{3-n}$     (I)

in which m is a number from 1 to 10;

n is 1, 2 or 3;

Z is an aliphatic hydrocarbon, phenylene, cycloaliphatic hydrocarbon, aliphatic-phenylene or aliphatic-cycloaliphatic radical having from one to about twenty carbon atoms;

A is selected from the group consisting of —NH and O; and

R is selected from the group consisting of hydrogen, alkyl having from one to about six carbon atoms, -R'NH$_2$ or -R'OH, where R'=alkylene having from one to about six carbon atoms.

In the case where A is NH and R is H, the amines have the formula:

[NH$_2$—Z]$_n$—NH$_{3-n}$     (II)

In the case where A is NH and R is alkyl, the amines have the formula:

[RNH—Z]$_n$—NH$_{3-n}$     (III)

In the case where A is O and R is H, the amines have the formula:

[HO—Z]$_n$—NH$_{3-n}$     (IV)

In the case where A is O and R is alkyl, the amines have the formula:

[RO—Z]$_n$—NH$_{3-n}$     (V)

In formulae II, III, IV and V,
n is 1, 2 or 3; and
In formulae III and V,
R is alkyl.

A particularly preferred class of amines has the formula:

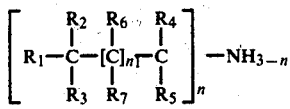
VI wherein
$R_1$ is selected from the group consisting of amino, hydroxyl, and alkoxy groups;

$R_2$, $R_3$, $R_4$, $R_5$, $R_6$ and $R_7$ are selected from the group consisting of hydrogen H, hydroxyl OH, amino $NH_2$, alkoxy, alkyl, hydroxyalkyl and aminoalkyl groups having from one to about six carbon atoms;

n is 1, 2 or 3; and $n_1$ is a number from 0 to about 10, preferably from 0 to 3.

When $R_1$ is $NH_2$ and n is 1, the amines have the formula:

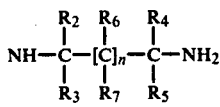
1.

When $R_1$ is OH the amines have the formula:

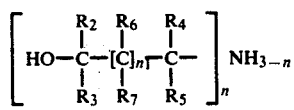
2.

When $R_1$ is alkoxy and n is 1, the amines have the formula:

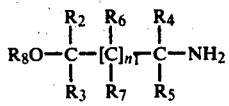
3.

wherein
$R_2$, $R_3$, $R_4$, $R_5$, $R_6$, $R_7$ and $n_1$ are as defined above in connection with Formula VI, and $R_8$ is lower alkyl having from one to five carbon atoms.

These amines can form the postulated unstable adduct via the amine group, and are stable under the reaction conditions.

Exemplary Z radicals, when Z is aliphatic, include straight chain and branched chain alkylene groups, which optionally may contain unsaturated groups, such as ethylenic $>C=C<$ and acetylenic $-C\equiv C-$ linkages, and have from two to about twenty carbon atoms. Exemplary Z alkylene groups include ethylene, propylene, butylene, pentylene, hexylene, heptylene, octylene, nonylene, decylene, undecylene, dodecylene, 2,2-dimethyl-propylene, 2-methyl-2-ethyl propylene, 2,2,4-trimethyl-butylene, 2,4-dimethyl-butylene, 2,4-dimethyl-pentylene, 2-methyl-propylene, 2,2-diethyl-propylene, 2,3-dimethyl-butylene, 2,3-diethyl-butylene, 2,3,4-trimethyl pentylene.

Exemplary cycloaliphatic Z radicals include cyclopentylene, cyclohexylene, cyclobutylene, cycloheptylene, cyclooctylene and cyclodecylene.

When Z is cycloalkylene or phenylene, the functional amino, hydroxyl or alkoxyl group is attached to the ring by way of an alkylene group having from one to about six carbon atoms, preferably methylene or ethylene.

Exemplary R alkyl radicals include methyl, ethyl, propyl, isopropyl, butyl, isobutyl sec-butyl, tert-butyl, amyl, isoamyl, sec-amyl, tert-amyl, neopentyl, hexyl, isohexyl, sec-hexyl, tert-hexyl 1,2-dimethyl butyl and neohexyl.

Exemplary R' alkylene radicals include methylene, ethylene, propylene, butylene, amylene, neopentylene, hexylene and neohexylene.

Exemplary polyamines falling within the above classes include ethylene diamine, propylene diamine, butylene diamine, pentylene diamine (pentamethylene diamine), hexylene diamine (hexamethylene diamine) octylene diamine, decylene diamine and dodecylene diamine. Exemplary aminoalcohols falling within the above classes include monoethanolamine, diethanolamine triethanolamine, propanolamine, butanolamine, dibutanolamine, dipropanolamine, tripropanolamine, tributanolamine, pentanolamine, hexanolamine, heptanolamine, octanolamine, nonanolamine, decanolamine, and dodecanolamine.

Exemplary aminoethers include methoxyethylamine, ethoxyethylamine, propoxyethylamine, butoxyethylamine, butoxybutylamine, propoxypropylamine, and ethoxyethyleneoxyethylamine.

The amine reacts stoichiometrically mole for mole, in forming the intermediate Adduct of Stage I. The breakdown of the adduct liberates one mole of free ketone, which would in turn form an imine if an excess of amine were present. At least two moles of amine per mole of prenyl-substituted methyl pentenones are necessary to convert all acetone and methyl heptenone to the imines. Of course, such conversion is perfectly acceptable, since the imines can be hydrolyzed with ease and the ketones (acetone and methyl heptenone) as well as the amine, recovered.

The ratio of amine to prenyl-substituted methyl pentenones for an efficient reaction should be within the range from about 0.2:1 to about 3:1. Smaller ratios such as 0.01:1 can be used if a slow and incomplete reaction is acceptable. On the other hand ratios of 10:1 or 20:1 or higher ratios can be used, but there is no practical advantage in doing so, other than an increased reaction rate.

The reaction in Stage I proceeds in the absence of base. In order however to increase the reaction rate and reduce the formation of prenyl-substituted methyl pentenone imine, a small amount of an inorganic alkali can be added, if desired.

As the inorganic alkali, there can be used any alkali metal hydroxide, such as sodium hydroxide and potassium hydroxide, and any alkaline earth metal hydroxide, such as calcium hydroxide, strontium hydroxide and barium hydroxide. Also useful are alkaline-reacting salts, such as the alkali metal and alkaline earth metal carbonates, bicarbonates, borates, tartrates, oxalates, acetates, formates and sulfites, for example, sodium carbonate, sodium bicarbonate, potassium carbonate, and potassium bicarbonate.

Each of the two stages of the process can be conducted over a wide temperature range, within the range from about 10° to about 250° C. Low temperatures mean lower operating costs and less material loss. However, longer reaction times are needed, so usually a balance is struck between the two. Since good yields at low operating cost are obtainable at temperatures within the range from about 70° to about 130° C., the preferred temperatures are within that range.

If prenyl-substituted methyl pentenone imine is present, a higher hydrolysis temperature may be required, since these imines are slow to hydrolyze at temperatures below 100° C.

Accordingly, a hydrolysis carried out by introduction of steam at temperatures of from about 100° to about 125° C. is particularly desirable. A steam distillation at this temperature to remove ketones as they are liberated in the course of the hydrolysis, including methyl heptenone, is especially suitable, since this helps drive the hydrolysis to completion while maintaining a high reaction temperature in the system.

The reaction proceeds at atmospheric pressure, but when reaction temperatures are employed above the boiling point of volatile ingredients in the reaction system the reaction can be carried out under a condenser, or in a pressure vessel, such as an autoclave. When an autoclave is used, high pressures may be developed without disadvantage, up to and including 1000 psi. Preferably, however, the reaction is carried out under a condenser or fractionating column at atmospheric pressure.

The reaction time depends upon the reaction temperature, the reactants, and the amine. The reaction proceeds well with good yields at reaction times that are normally less than four hours, and frequently less than two hours, but in some cases a longer reaction time may be required, up to eight to twelve hours.

If an inorganic alkali is employed in the first stage of the reaction it is added as a solid and the amount can be very small. The alkali concentration in this phase can be within the range from about 0.05 to about 2% by weight, and preferably from about 0.1 to about 1%. While more alkali can be used, there is no benefit, and large amounts are therefore uneconomic, but amounts as high as 60% can be used.

In Stage I of the reaction, depending on conditions, free methyl heptenone can be found and isolated. However, hydrolysis of methyl heptenone imine gives a further increment of methyl heptenone, and is desirable for higher conversion efficiency. Thus a hydrolysis stage by addition of water to the reaction mixture is a preferred embodiment of the process of the invention.

Water added for the hydrolysis stage forms a separate phase with the prenyl-substituted methyl pentenone mixture. The two phases are brought into contact during the hydrolysis reaction by stirring, or other conventional mixing technique.

The water used in Stage II reacts stoichiometrically with any imines present in the reaction mixture of Stage I but an excess of water causes no problems, except in the cost of handling unnecessarily large amounts of water. Therefore, approximately stoichiometric amounts of water are also used. The stoichiometric amount is of course based on the total imine content of the reaction system.

The process is ideally suited for a continuous mode of operation, if in the first stage prenyl-substituted methyl pentenones and amine are mixed together and in the second stage the above stream is treated with water, whereby acetone and methyl heptenone are continuously withdrawn. The amine is recycled as it is regenerated.

The process can also be carried out in a batchwise manner in which event the amounts of ketone and amine can be stoichiometric, or above or below this amount. Of course, larger amounts of amine can be added.

The following Examples in the opinion of the inventors represent preferred embodiments of the invention.

EXAMPLES 1 and 2

These Examples illustrate the process of the invention using various prenyl mesityl oxide mixtures. The prenyl mesityl oxide used as a starting material in Example 1 was essentially the nonconjugated isomer (98%) with 2% of the conjugated isomer. The prenyl mesityl oxide of Example 2 on the other hand was 97% conjugated isomer and 2.3% nonconjugated isomer.

One gram samples of prenyl mesityl oxide were combined with 1 g of ethanolamine and sealed in a reaction vessel, which was then left at room temperature (25° C.) for ten days. The composition of the mixture was determined by vapor phase chromatography.

The results obtained are shown in Table I.

TABLE I

|  | Example 1 % | Example 2 % |
|---|---|---|
| 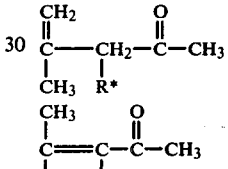 | 19.3 | 4.7 |
| 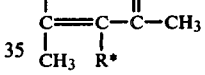 | 2.2 | 3.7 |
| Prenyl mesityl oxide imine | 46.5 | 5.8 |
| Acetone | 3.8 | 9.3 |
| Acetone imine | 4.1 | 21.9 |
| Methyl heptenone | 6.9 | 28.8 |
| Methyl heptenone imine | 1.2 | 15.6 |

*R = prenyl

The results of Example 1 suggest that imine formation at room temperature proceeds via the nonconjugated prenyl mesityl oxide isomer. Methyl heptenone and methyl heptenone imine represent only 6.9 to 1.2%, respectively, with 19.3% nonconjugated prenyl mesityl oxide unchanged.

Example 2 shows that the conjugated prenyl mesityl oxide isomer reacts more rapidly to form methyl heptenone; the amount of prenyl mesityl oxide imine is lower (5.8%). It is apparent that there is some interconversion of the isomers, leading to a change in the proportions of the two isomers. Methyl heptenone and methyl heptenone imine as well as acetone and acetone imine represent the major products, indicating that reaction with the amine to form the amine adduct product involves mostly the conjugated isomer.

Hydrolysis of the reaction products from each Example with water yields methyl heptenone that can be recovered and prenyl mesityl oxide that can be recycled.

EXAMPLES 3 and 4

20 g of prenyl mesityl oxide was mixed with 8 g ethanolamine, and also with 0.2 g sodium hydroxide as fine beads in Example 4, placed in closed bottles, and heated at 105° C. Samples were taken after one, two and three hours. The gas-liquid chromatographic analysis of these samples shown in Table II indicates the reaction rate and the distribution of the various products. Example 4 with sodium hydroxide gave a faster reaction, with less prenyl mesityl oxide imine in the product.

EXAMPLES 8 to 15

In each of these Examples 100 g prenyl mesityl oxide (PMO) was combined with 40 g ethanolamine and alkali as indicated in the Table, and the mixtures heated at the

TABLE II

| Example No. | Time (hours) | % Acetone | % Acetone Imine | % Methyl Heptenone | % Methyl Heptenone Imine | % Unreacted Prenyl Mesityl Oxide | % Prenyl Mesityl Oxide Imine |
|---|---|---|---|---|---|---|---|
| 3 | 1 | 2.7 | 12.9 | 9.5 | 17.2 | 38.8 | 18.5 |
|   | 2 | 4.6 | 12.7 | 15.0 | 18.7 | 22.2 | 24.6 |
|   | 3 | 4.5 | 14.9 | 16.9 | 20 | 20 | 24.4 |
| 4 | 1 | 6.4 | 21.0 | 25.5 | 23.1 | 15.3 | 5.2 |
|   | 2 | 7.9 | 21.5 | 28.0 | 26.2 | 8.3 | 5.2 |
|   | 3 | 7.9 | 17.5 | 30.7 | 27.7 | 4.5 | 4.5 |

Each of the reaction products was shaken with 50 g of water at room temperaure for one hour and acetone imine and methyl heptenone imine were hydrolyzed to the corresponding ketones. Prenyl mesityl oxide imine remained, as it hydrolyzes very slowly at room temperature.

EXAMPLE 5 to 7

Prenyl mesityl oxide (20 g 13% nonconjugated, 79.7% conjugated isomer) and ethanolamine (in the three Examples 8, 16 and 32 g respectively) were mixed and heated at 106°-107° C. for two hours, until all mixtures were homogeneous. Analysis of samples taken after one and two hours heating indicate the composition of the reaction products prior to hydrolysis. The results are given in Table III.

temperatures and for the times indicated in Table IV below, under agitation.

Samples taken from the reaction mixtures during the reaction and analyzed by gas chromatography indicate the ratio of the various intermediates as well as the amount of unreacted prenyl mesityl oxide.

The reaction mixtures were subjected to steam distillation using steam at 100°-125° C., hydrolyzing the imines present and distilling out the ketones, such as acetone, methyl heptenone and prenyl mesityl oxide. The methyl heptenone is recovered from the distillate by fractional distillation. Ethanolamine is recovered from the pot residue after steam distillation.

TABLE IV

|  | Inorganic Alkali | | Pot Temp °C. | Time Hours | Analysis | | | | | | After Hydrolysis | | | True Yield % |
|---|---|---|---|---|---|---|---|---|---|---|---|---|---|---|
|  | Type | Grams | | | PMO | PMO I | AC | AC I | MH | MHI | M. Hept. g | PMO g | Direct Yield % | |
| Example 8 | NaOH | 1.0 | 112-120 | 2.5 |  |  |  |  |  |  | 55.1 | 2.2 | 76.3 | 78.1 |
| Example 9 | Ba(OH)₂. 6 H₂O | 1.0 | 93-115 | 3.5 | 18.4 | 11.5 | 3.3 | 13.5 | 23.8 | 29.5 | ← | No | hydrolysis | → |
|  |  |  |  | 21.0 | 8.2 | 10.6 | 7.1 | 19.1 | 26.6 | 28.4 | ← | No | hydrolysis | → |
| Example 10 | NaOH | 0.5 | 114-124 | 1.0 | 11.0 | 7.1 | 6.3 | 20.6 | 25.7 | 32.8 | ← | No | hydrolysis | → |
|  |  |  |  | 2.0 | 5.7 | 5.9 | 4.2 | 18.2 | 23.6 | 41.9 | ← | No | hydrolysis | → |
|  |  |  |  | 4.0 | — | 5.1 | 4.8 | 19.3 | 24.8 | 44.9 | 62.8 |  | — 86.9 | 86.9 |
| Example 11 | NaOH | 0.25 | 110-120 | 3.0 | 6.3 | 5.3 | 8.4 | 21.6 | 28.0 | 26.7 |  | 5.3 | 81.7 | 89.6 |
| Example 12 | K₂CO₃ | 1.0 | 108-119 | 1.0 | 25.9 | 12.0 | 4.9 | 16.4 | 20.3 | 27.4 | ← | No. | hydrolysis | → |
| Example 13 | NaOH | 0.5 | 104 | 2.0 | 9.9 | 6.0 | 7.2 | 19.7 | 24.7 | 26.0 | ← | No | hydrolysis | → |
|  |  |  |  | 3.0 | 6.2 | 5.5 | 8.4 | 19.7 | 27.1 | 26.5 |  |  |  |  |
|  |  |  |  | 4.0 | 3.8 | 4.5 | 7.3 | 21.2 | 25.5 | 30.5 | 59.4 |  | 4.9 83.5 | 86.4 |
| Example 14 | NaOH | 0.5 | 104 | 2.0 | 9.9 | 6.1 | 7.3 | 20.3 | 24.7 | 26.6 |  |  |  |  |
|  |  |  |  | 4.5 | 4.5 | 5.1 | 7.0 | 13.4 | 25.0 | 32.0 | 69.8 |  | 2.5 98.0 | 100.0 |
| Example 15 | NaOH | 0.5 | 85-90 | 2.75 | 14.3 | 6.0 | 7.0 | 18.1 | 24.6 | 23.0 |  |  |  |  |
|  |  |  |  | 5.75 | 9.7 | 5.5 | 6.7 | 17.5 | 26.1 | 28.0 | 61.4 |  | 6.6 86.3 | 92.8 |

PMO = Prenyl Mesityl Oxide
PMO I = Prenyl Mesityl Oxide Imine
AC = Acetone
AC I = Acetone Imine
MH = Methyl Heptenone
MHI = Methyl Heptenone Imine It is apparent from the above data that a hydrolysis is not essential to obtain a good yield of methyl heptenone. Hydrolysis does nowever considerably improve yield and efficient, in reducing the amounts of material recycled for further reaction.

TABLE III

| Example No. | Time (hours) | % Acetone | % Acetone Imine | % Methyl Heptenone | % Ethanol Amine | % Prenyl Mesityl Oxide[1] | % Methyl Heptenone Imine | % Prenyl Mesityl Oxide Imine |
|---|---|---|---|---|---|---|---|---|
| 5 | 1 | 1.6 | 11.5 | 6.9 | 9.2 | 31.7 | 14.6 | 20.6 |
|   | 2 | 2.5 | 12.7 | 8.7 | 10.0 | 24.1 | 16.1 | 23.3 |
| 6 | 1 | 1.4 | 14.6 | 4.8 | 24.5 | 7.8 | 19.7 | 22.0 |
|   | 2 | 1.9 | 15.2 | 5.0 | 23.7 | 5.5 | 22.0 | 22.3 |
| 7 | 1 | 0.9 | 12.2 | 2.4 | 42 | 1.1 | 17.5 | 17.5 |
|   | 2 | 0.8 | 12.3 | 1.8 | 45.7 | 0.6 | 20.3 | 15.9 |

[1]Mixture of conjugated and nonconjugated isomers

EXAMPLE 16

A 500 ml flask was charged with 100.0 g of prenyl mesityl oxide (13% nonconjugated 79.7% conjugated isomer), 0.56 mole, 40.6 g ethylene diamine, and 0.5 g NaOH. This was then flushed thoroughly with nitrogen. The mixture was heated at between 95° and 105° C. and agitated for approximately four hours under a slight nitrogen pressure. Analysis by gas liquid chromatography indicated that 31.9% prenyl mesityl oxide remained unchanged after this time. Steam distillation of the pot mixture gave a true yield of 95.8% of methyl heptenone based on the prenyl mesityl oxide reacted, after the recovery of unreacted prenyl mesityl oxide.

EXAMPLE 17

100 g of prenyl mesityl oxide (78% conjugated isomer and 13% nonconjugated isomer) was stirred for five hours at 115°-120° C. with 42 g of 1,3-propylene diamine and 0.5 g NaOH. After hydrolysis by submitting the reaction mixture to steam distillation, methyl heptenone 62.6 g and unreacted prenyl mesityl oxide 6.9 g were recovered.

Having regard to the foregoing disclosure, the following is claimed as the inventive and patentable embodiments thereof:

1. A process for preparing methyl heptenone from a ketone mixture comprising prenyl-substituted methyl pentenones, which comprises reacting the ketone mixture with an amine having at least two functional groups, of which at least one group is an amine group and the other group is selected from the group consisting of another amine group, a hydroxyl group and an alkoxy group, at a temperature within the range from about 10° to about 250° C.; and then recovering methyl heptenone from the reaction mixture.

2. A process according to claim 1 in which the amine has the formula:

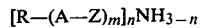

in which
m is a number from 1 to 10;
n is 1, 2 or 3;
Z is selected from the group consisting of aliphatic hydrocarbon, phenylene, cycloaliphatic hydrocarbon, aliphatic hydrocarbon-phenylene and aliphatic-cycloaliphatic hydrocarbon radicals having from one to about twenty carbon atoms;
A is selected from the group consisting of —NH and O; and
R is selected from the group consisting of hydrogen, alkyl having from one to about six carbon atoms, —R'$NH_2$ and —R'OH, where R' is alkylene having from one to about six carbon atoms.

3. A process according to claim 2, in which R is hydrogen and A is NH.

4. A process according to claim 2, in which R is alkyl and A is NH.

5. A process according to claim 2, in which R is hydrogen and A is —O—.

6. A process according to claim 2, in which R is alkyl and A is —O—.

7. A process according to claim 2, in which the amine has the formula:

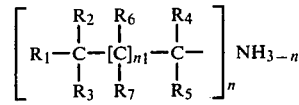

wherein
$R_1$ is selected from the group consisting of amino, hydroxyl, and alkoxy groups;
$R_2$, $R_3$, $R_4$, $R_5$, $R_6$ and $R_7$ are selected from the group consisting of hydrogen H, hydroxyl OH, amino $NH_2$, alkoxy, alkyl, hydroalkyl and aminoalkyl groups having from one to about six carbon atoms;
n is 1, 2 or 3; and
$n_1$ is a number from 0 to about 10.

8. A process according to claim 7, in which $R_1$ is $NH_2$ and n is 1.

9. A process according to claim 8, in which $R_2$, $R_3$, $R_4$ and $R_5$ are H and $n_1$ is 0.

10. A process according to claim 7, in which $R_1$ is OH and n is 1.

11. A process according to claim 10, in which $R_2$, $R_3$, $R_4$, $R_5$ are H and $n_1$ is 0.

12. A process according to claim 11, in which $R_2$, $R_3$, $R_4$, $R_5$ are H, $n_1$ is 0, and R' is methyl or ethyl.

13. A process according to claim 7, in which $R_1$ is OH and n is 2.

14. A process according to claim 7, in which $R_1$ is OH and n is 3.

15. A process according to claim 1, in which an inorganic alkali is present during the reaction of ketone with amine.

16. A process according to claim 15, in which the inorganic alkali is an alkali metal or alkaline earth metal hydroxide.

17. A process according to claim 15, in which the inorganic alkali is an alkali metal or alkaline earth metal alkaline salt.

18. A process according to claim 1, which comprises hydrolyzing the reaction product of amine and ketone mixture with water to decompose ketone imines to free ketones.

19. A process according to claim 18, in which an inorganic alkali is also present during the hydrolysis.

20. A process according to claim 18 in which the hydrolysis is effected in the course of steam distillation of volatile ketones from the reaction mixture.

21. A process according to claim 18, in which the hydrolysis temperature is within the range from about 100° to about 125° C.

22. A process according to claim 18, in which the hydrolysis is carried out at atmospheric pressure.

23. A process according to claim 18, in which the hydrolysis is carried out at an elevated pressure up to 1000 psi.

24. A process according to claim 18, in which methyl heptenone and acetone are separated together from the hydrolysis reaction as the reaction proceeds.

25. A process according to claim 18, in which the prenyl-substituted methyl pentenones and amine are blended continuously in a reaction zone, held in the zone for a reaction dwell time, and reaction product continuously withdrawn from the reaction zone, then to the withdrawn reaction product water is continuously added, and volatile ketone hydrolysis product continuously distilled out of the hydrolysis reaction mixture.

26. A process according to claim 25, in which the water is added as steam, and methyl heptenone and acetone steam-distilled out of the hydrolysis reaction mixture as the reaction proceeds.

27. In the process for preparing methyl heptenone from acetone which comprises reacting acetone at a temperature within the range from about −20° to about 150° C. with prenyl chloride in the presence of solid alkali metal hydroxide selected from the group consisting of potassium hydroxide, sodium hydroxide, and mixtures thereof, and as a catalyst a nitrogen compound which is selected from the group consisting of ammonia and aliphatic, cycloaliphatic and heterocyclic hydrocarbon amines having from one to about sixty carbon atoms, such hydrocarbon amines containing hydroxy substituents, such hydrocarbon amines containing carboxylic acid substituents, and such hydrocarbon amines containing nitro-substituents; the amounts of the acetone and prenyl chloride being in the molar ratio of from about 1:5 to about 20:1, the alkali metal hydroxide being in the proportion of from about 1 to about 2 moles per mole of prenyl chloride, and the amount of nitrogen compound being within the range from about 0.003 mole to about 1 mole per mole of prenyl chloride, the improvement which comprises separating methyl heptenone from the reaction mixture comprising prenyl-substituted methyl pentenones; reacting the prenyl-substituted methyl pentenones with an amine having at least two functional groups, of which at least one group is an amine group and the other group is selected from the group consisting of another amine group, a hydroxyl group and an alkoxy group, at a temperature within the range from about 10° to about 250° C.; and then subjecting the reaction product to hydrolysis with water; and recovering methyl heptenone from the hydrolysis reaction mixture.

28. A process according to claim 27, in which the reaction with amine and the hydrolytic cracking are carried out in the presence of inorganic alkali.

29. A process in accordance with claim 28, in which a mixture of mesityl oxide and acetone is reacted with the prenyl chloride.

30. In the process for preparing methyl heptenone from mesityl oxide which comprises reacting mesityl oxide at a temperature within the range from about −20° to about 150° C. with prenyl chloride in the presence of solid alkali metal hydroxide selected from the group consisting of potassium hydroxide, sodium hydroxide, and mixtures thereof, and as a catalyst a nitrogen compound which is selected from the group consisting of ammonia and aliphatic, cycloaliphatic and heterocyclic hydrocarbon amines having from one to about sixty carbon atoms, such hydrocarbon amines containing hydroxy substituents, such hydrocarbon amines containing carboxylic acid substituents, and such hydrocarbon amines containing nitro substituents; the amounts of the mesityl oxide and prenyl chloride being in the molar ratio of from about 1:5 to about 20:1, the alkali metal hydroxide being in the proportion of from about 1 to about 2 moles per mole of prenyl chloride, and the amount of nitrogen compound being within the range from about 0.003 mole to about 1 mole per mole of prenyl chloride; the improvement which comprises separating from the reaction mixture a fraction comprising phenyl-substituted methyl pentenones; reacting the prenyl-substituted methyl pentenone fraction with an amine having at least two functional groups, of which at least one group is an amine group and the other group is selected from the group consisting of another amine group, a hydroxyl group and an alkoxy group, at a temperature within the range from about 10° to about 250° C.; and then subjecting the reaction product to hydrolysis with water, and recovering methyl heptenone from the hydrolysis reaction mixture.

31. A process according to claim 30, in which the reaction with amine and the hydrolysis are carried out in the presence of inorganic alkali.

32. A process according to claim 1 in which the proportion of amine to prenyl-substituted methyl pentenones is within the range from about 0.9:1 to about 1:1 to 1.

33. A process according to claim 1 in which the amine is in an amount within the range from 25 to 40 g amine per 100 g prenyl-substituted methyl pentenones.

34. A process according to claim 1 in which the water is in a stoichiometric amount based on the total imine content of the reaction system.

* * * * *

UNITED STATES PATENT AND TRADEMARK OFFICE
CERTIFICATE OF CORRECTION

PATENT NO. : 4,153,633

DATED : May 8, 1979

INVENTOR(S) : Peter S. Gradeff et al

It is certified that error appears in the above-identified patent and that said Letters Patent are hereby corrected as shown below:

Column 2, line 43 : "prepared" should be --prepare--
Column 14, line 54 : "nowever" should be --however--
Column 6, line 29 :
Reaction A

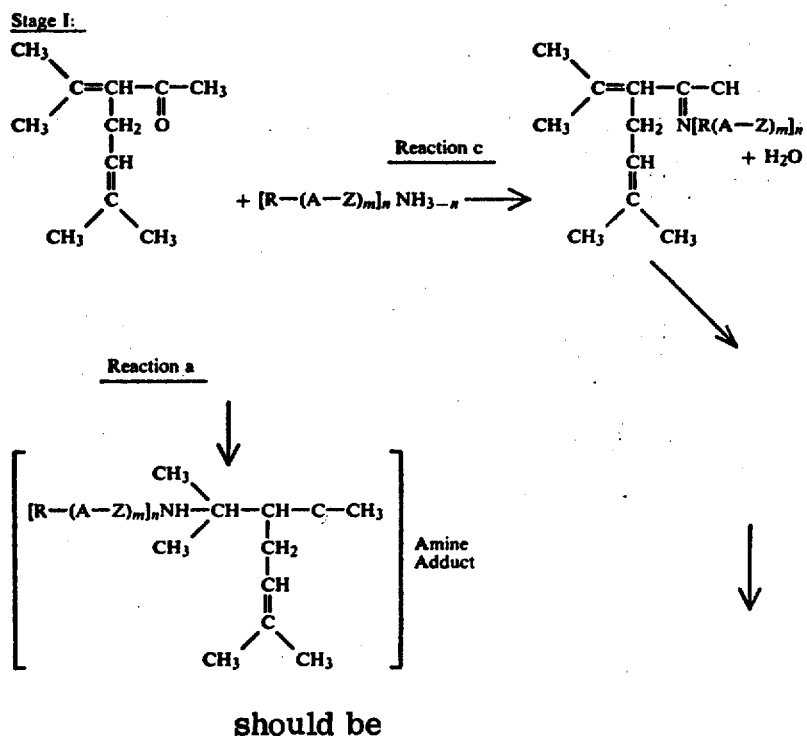

should be

UNITED STATES PATENT AND TRADEMARK OFFICE
CERTIFICATE OF CORRECTION

PATENT NO. : 4,153,633
DATED : May 8, 1979
INVENTOR(S) : Peter S. Gradeff et al

Page 2 of 2

It is certified that error appears in the above-identified patent and that said Letters Patent are hereby corrected as shown below:

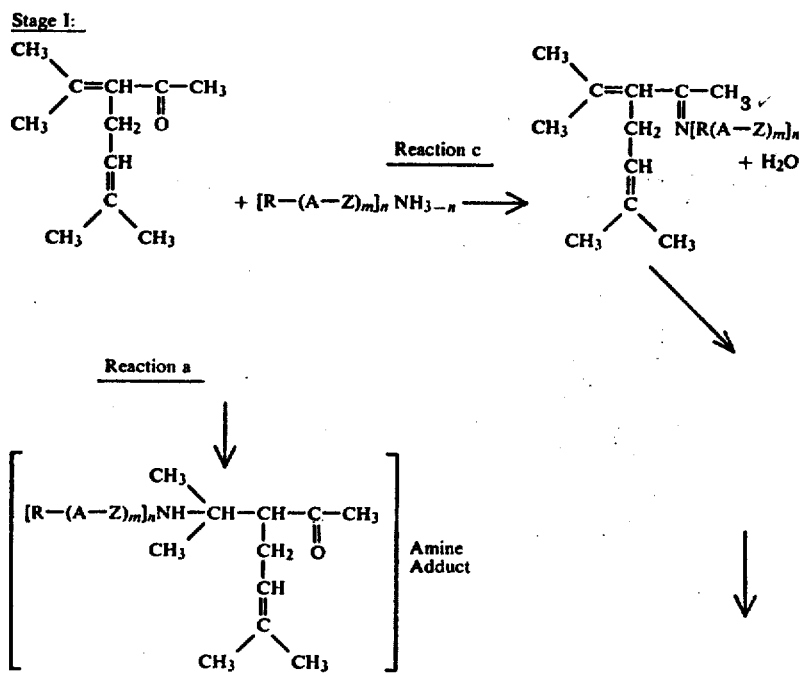

Signed and Sealed this

Twenty-second Day of January 1980

[SEAL]

Attest:

SIDNEY A. DIAMOND

Attesting Officer

Commissioner of Patents and Trademarks